(12) United States Patent
Loo et al.

(10) Patent No.: US 11,616,333 B2
(45) Date of Patent: Mar. 28, 2023

(54) ENDOSCOPE DEVICE AND CABLE ASSEMBLY THEREOF

(71) Applicant: ALTEK BIOTECHNOLOGY CORPORATION, Hsinchu (TW)

(72) Inventors: Hsi-Hsin Loo, Hsinchu (TW); Parn-Far Chen, Hsinchu (TW); Liang-Yi Li, Hsinchu (TW); Chao-Yu Chou, Hsinchu (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 322 days.

(21) Appl. No.: 16/558,242

(22) Filed: Sep. 2, 2019

(65) Prior Publication Data

US 2020/0194951 A1    Jun. 18, 2020

(30) Foreign Application Priority Data

Dec. 12, 2018 (TW) ................. 107216874

(51) Int. Cl.
*H01R 43/02* (2006.01)
*H01R 12/53* (2011.01)
(Continued)

(52) U.S. Cl.
CPC .............. *H01R 43/02* (2013.01); *A61B 1/05* (2013.01); *A61B 1/0661* (2013.01); *H01R 12/53* (2013.01); *H05K 3/34* (2013.01)

(58) Field of Classification Search
CPC ............ A61B 1/00018; A61B 1/00114; A61B 1/00124; A61B 1/05; A61B 1/051;
(Continued)

(56) References Cited

U.S. PATENT DOCUMENTS

2004/0147807 A1* 7/2004 Viebach ............... A61B 1/0008
600/129
2006/0109368 A1* 5/2006 Ayrenschmalz ..........................
H01L 27/14636
348/340

(Continued)

FOREIGN PATENT DOCUMENTS

| CN | 101145642 A | 3/2008 |
|---|---|---|
| TW | I606642 B | 11/2017 |
| TW | M564312 U | 7/2018 |

*Primary Examiner* — Aaron B Fairchild
*Assistant Examiner* — Stephen Floyd London
(74) *Attorney, Agent, or Firm* — Li & Cai Intellectual Property (USA) Office

(57) ABSTRACT

An endoscope device and a cable assembly thereof are provided. The cable assembly includes a first substrate, a second substrate, and a wire. The first substrate includes a first body and a first solder pad disposed on the first body. The second substrate is correspondingly disposed on the first substrate and includes a second body, a second solder pad disposed on the second body and corresponding to the first solder pad, and an accommodating portion corresponding to the second solder pad. The wire includes a soldering portion disposed in the accommodating portion. The first solder pad and the second solder pad are coupled to each other by at least one of a first solder and a second solder, and the soldering portion and the second solder pad are coupled to each other by the first solder.

4 Claims, 16 Drawing Sheets

(51) Int. Cl.
  *A61B 1/06* (2006.01)
  *A61B 1/05* (2006.01)
  *H05K 3/34* (2006.01)

(58) Field of Classification Search
  CPC ....... A61B 1/053; A61B 1/015; A61B 1/0011; A61B 1/00119; H01R 9/0509; H05K 2201/041; H05K 2201/09027; H05K 2201/09463
  USPC ........................................................ 600/110
  See application file for complete search history.

(56) References Cited

U.S. PATENT DOCUMENTS

| | | | |
|---|---|---|---|
| 2008/0055403 A1* | 3/2008 | Salman | A61B 1/05 348/76 |
| 2008/0255416 A1* | 10/2008 | Gilboa | H04N 5/232 600/110 |
| 2012/0029287 A1* | 2/2012 | Wieters | H01B 17/305 600/133 |
| 2012/0206583 A1* | 8/2012 | Hoshi | H04N 5/2253 348/76 |
| 2015/0098237 A1* | 4/2015 | Motohara | G02B 6/423 362/554 |
| 2015/0342530 A1* | 12/2015 | Dekker | A61B 1/0684 600/478 |
| 2016/0029879 A1* | 2/2016 | Ishikawa | G02B 23/2484 600/110 |
| 2018/0008132 A1* | 1/2018 | Sakai | A61B 1/00013 |
| 2018/0070799 A1* | 3/2018 | Sekido | A61B 1/0011 |
| 2018/0249896 A1* | 9/2018 | Mikami | H01B 11/002 |
| 2018/0325364 A1* | 11/2018 | Okamura | H01L 27/14636 |
| 2020/0000328 A1* | 1/2020 | Sakai | A61B 1/00018 |
| 2021/0037169 A1* | 2/2021 | Numasawa | A61B 1/06 |

* cited by examiner

ENDOSCOPE DEVICE AND CABLE ASSEMBLY THEREOF

CROSS-REFERENCE TO RELATED PATENT APPLICATION

This application claims the benefit of priority to Taiwan Patent Application No. 107216874, filed on Dec. 12, 2018. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to an endoscope device and a cable assembly thereof, and more particularly to an endoscope device and a cable assembly capable of the endoscope device which can firmly solder a wire.

BACKGROUND OF THE DISCLOSURE

Since a conventional endoscope is a tubular structure and has a small cross section, in order to solder a signal wire to a circuit board provided with an image sensor or a photosensitive member, the signal wire will inevitably be soldered to the circuit board in a vertical soldering manner. However, when a wire is vertically welded to a circuit board having a diameter of less than 5 mm (millimeter, mm), the solder quality can easily be compromised. One of the conventional solutions is to bend an inner conductor of the signal wire at 90 degrees and solder the bent inner conductor on the circuit board in parallel. However, this method requires a large welding area and a cable space, and is difficult to be operated.

SUMMARY OF THE DISCLOSURE

In response to the above-referenced technical inadequacies, the present disclosure provides an endoscope device and a cable assembly thereof.

In one aspect, the present disclosure provides a cable assembly including: a first substrate, a second substrate, and a wire. The first substrate includes a first body and a first solder pad disposed on the first body. The second substrate correspondingly disposed on the first substrate includes a second body, a second solder pad disposed on the second body and corresponding to the first solder pad, and an accommodating portion corresponding to the second solder pad. The wire includes a soldering portion disposed in the accommodating portion. The first solder pad and the second solder pad are coupled to each other by at least one of a first solder and a second solder, and the soldering portion and the second solder pad are coupled to each other by the first solder.

In one aspect, the present disclosure provides an endoscope device including: a shell body, a cable assembly, an image sensor, and an LED element. The cable assembly is disposed in the shell body, and includes a first substrate, a second substrate, and a wire. The first substrate includes a first body and a first solder pad disposed on the first body. The second substrate includes a second body, a second solder pad disposed on the second body and corresponding to the first solder pad, and an accommodating portion corresponding to the second solder pad. The wire includes a soldering portion disposed in the accommodating portion. The first solder pad and the second solder pad are coupled to each other by at least one of a first solder and a second solder, and the soldering portion and the second solder pad are coupled to each other by the first solder. The image sensor is disposed in the shell body, and the image sensor is disposed on the first substrate of the cable assembly and coupled to the first substrate. The light-emitting element is disposed in the shell body, and the light-emitting element is disposed on the first substrate of the cable assembly and coupled to the first substrate.

Therefore, one of the beneficial effects of the endoscope device and the cable assembly thereof of the present disclosure has the technical features of "the second substrate being correspondingly disposed on the first substrate and including a second body, a second solder pad disposed on the second body and corresponding to the first solder pad, and an accommodating portion corresponding to the second solder pad," and "the first solder pad and the second solder pad being coupled to each other by at least one of a first solder and a second solder, and the soldering portion and the second solder pad being coupled to each other by the first solder," so as to improve the reliability of the coupling effect between the wire and the first substrate.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
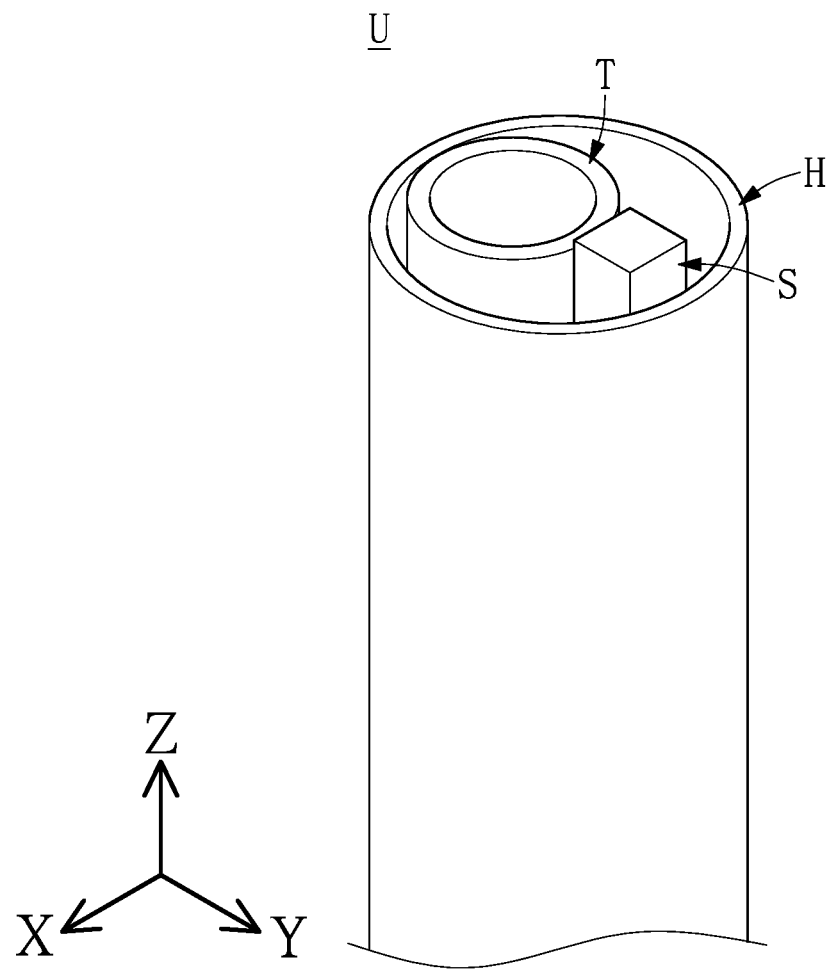
FIG. 1 is a perspective view of an endoscope device according to embodiments of the present disclosure.
Figure 2:
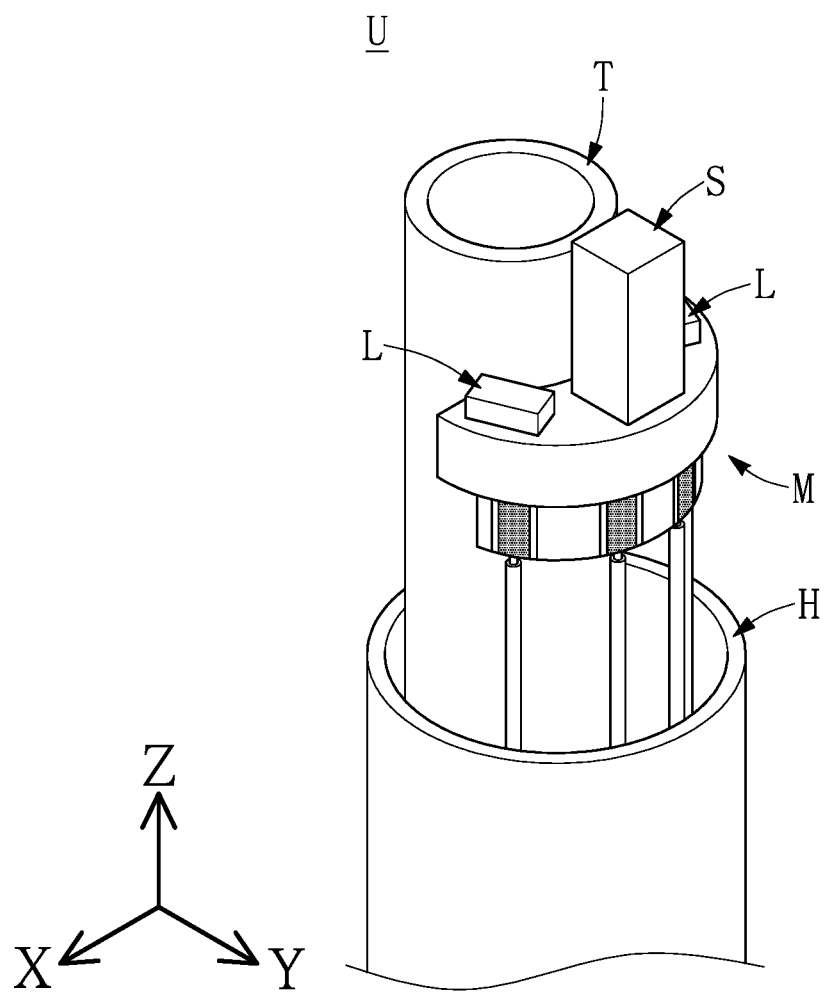
FIG. 2 is another perspective view of the endoscope device according to the embodiments of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 3:
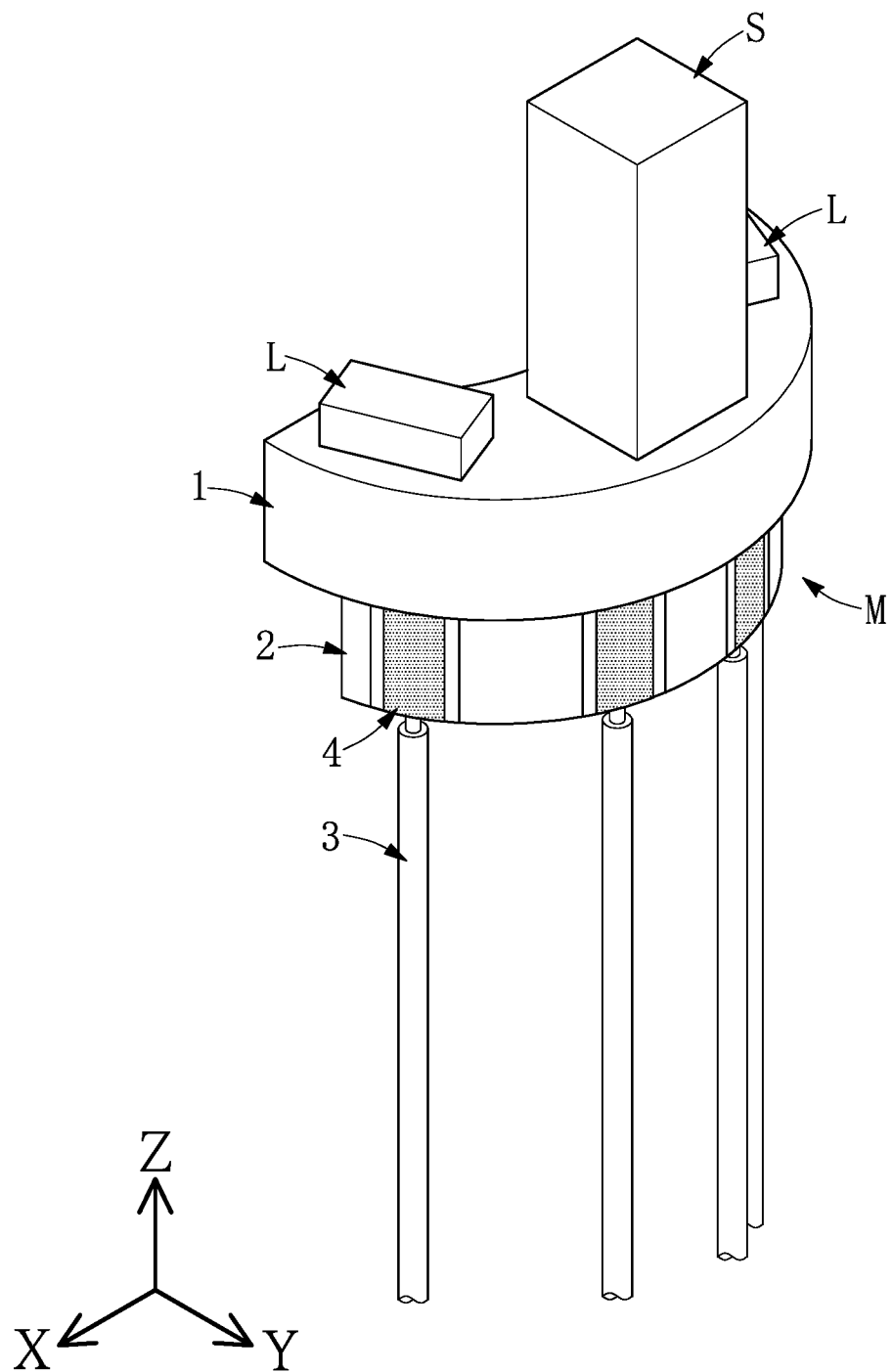
FIG. 3 is a perspective view of a cable assembly according to a first embodiment of the present disclosure.
Figure 4:
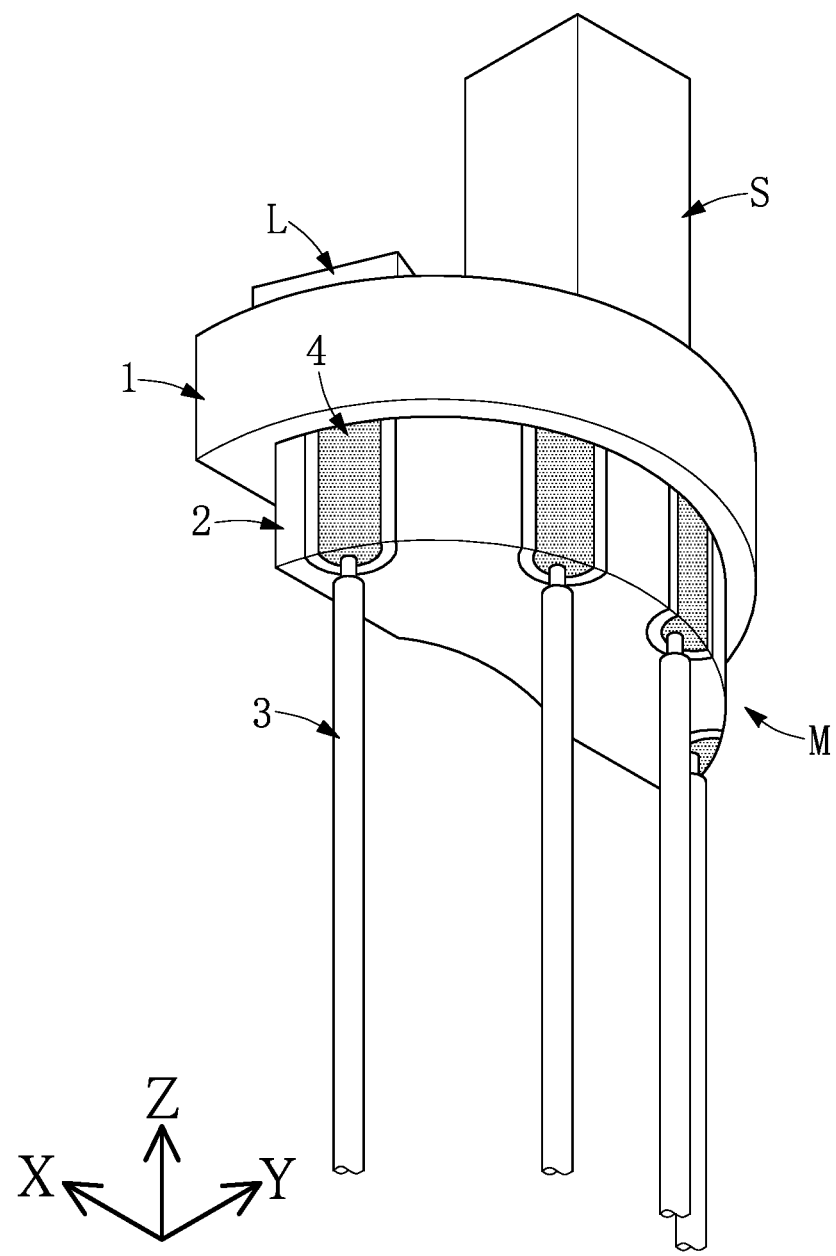
FIG. 4 is another perspective view of the cable assembly according to the first embodiment of the present disclosure.

Referring to FIG. 1 to FIG. 4, FIG. 1 and FIG. 2 are perspective views of an endoscope device according to embodiments of the present disclosure, and FIG. 3 and FIG. 4 are perspective views of a cable assembly of a first embodiment of the present disclosure. The present disclosure provides an endoscope device U and its cable assembly M. The main structure of the endoscope device U will be explained first, and the structure of the cable assembly M will be explained later. However, it should be noted that although the present embodiment is exemplified by the application of the cable assembly M to the endoscope device U, in other embodiments, the cable assembly M provided by the present disclosure can also be applied to other devices. The present disclosure is not limited to the applications of the cable assembly M disclosed herein.

As described above, referring to FIG. 1 to FIG. 4, the endoscope device U may include a shell body H, the cable assembly M, an image sensor S and one or more light-emitting element L. In addition, in a preferred embodiment, the endoscope device U may further include a working channel T. Further, the cable assembly M, the image sensor S, the light-emitting element L, and the working channel T can be set in the shell body H. In addition, the image sensor S can be, for example, but not limited to, a Charge Coupled Device (CCD) or a Complementary Metal-Oxide Semiconductor (CMOS). Further, the Light-emitting element L may be, for example, but not limited to, a light-emitting diode (LED). In addition, the working channel T can be used for medical devices to access and perform operations.

As described above, referring to FIG. 2 to FIG. 4, the cable assembly M may include a first substrate 1, a second substrate 2, and one or more wires 3. The wire 3 can be soldered to the second substrate 2 by a first solder 4 (such as, but not limited to, tin solder or solder paste) and indirectly coupled to the first substrate 1 via the second substrate 2. In addition, the image sensor S and the light-emitting element L may be disposed on the first substrate 1 of the cable assembly M and coupled to the first substrate 1 to enable the image sensor S and/or the light-emitting element L to receive signals from the wire 3 through the first substrate 1 and the second substrate 2.

Figure 5:
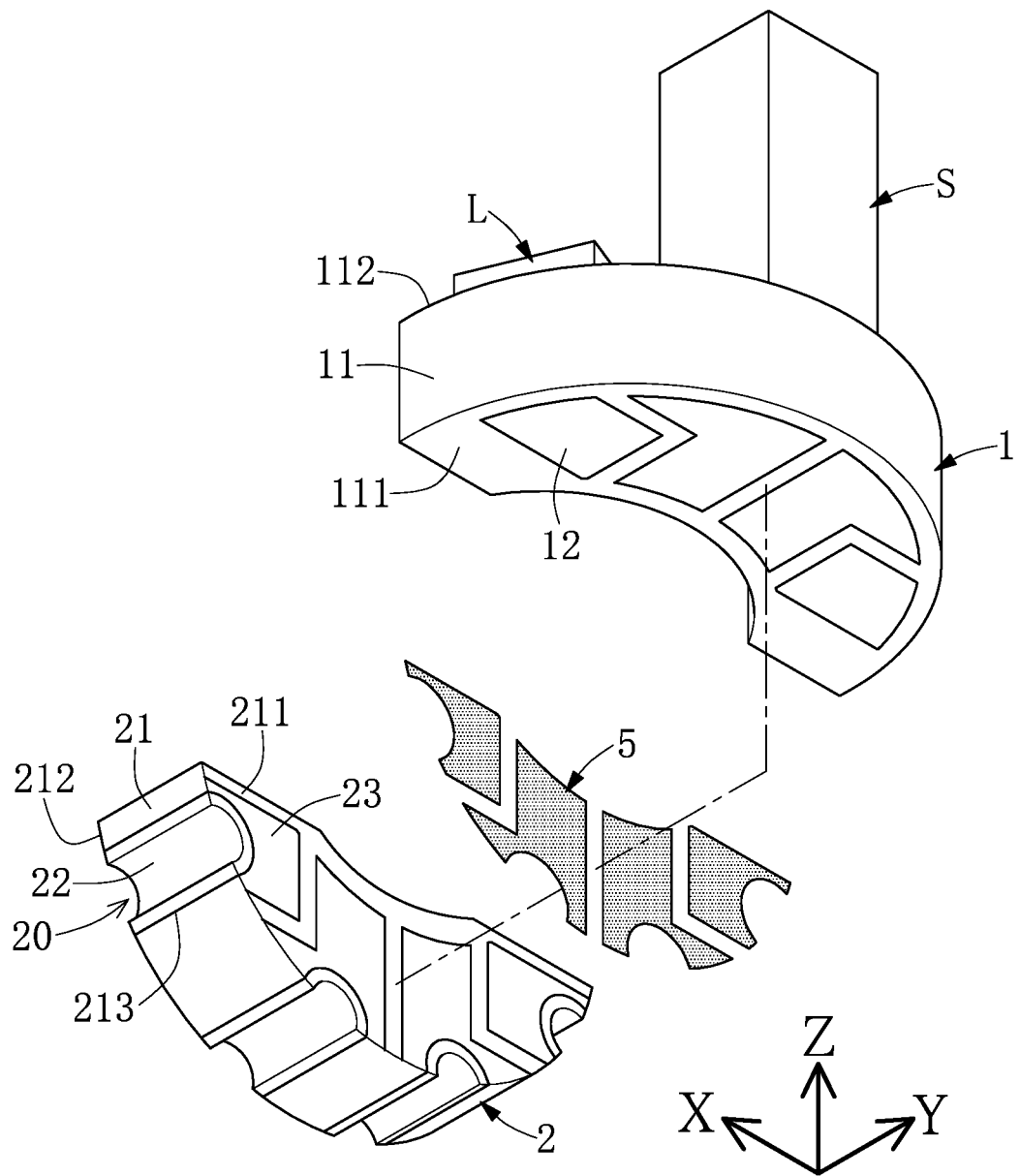
FIG. 5 is a perspective exploded view of the cable assembly according to the first embodiment of the present disclosure.

Next, referring to FIG. 3 and FIG. 4, and referring to FIG. 5 together, FIG. 5 is a perspective exploded view of the cable assembly according to the first embodiment of the present disclosure. The first substrate 1 may include a first body 11 and one or more first solder pads 12 disposed on the first body 11. The first body 11 may include a first surface 111 and a second surface 112 corresponding to the first surface 111. The first solder pad 12 may be disposed on the first surface 111. In addition, it should be noted that the second surface 112 may also be disposed with a plurality of conductive pads (not shown). The image sensor S and the light-emitting element L may also be disposed on the second surface 112 of the first body 11, and the image sensor S and the light-emitting element L may also be soldered to the conductive pads on the second surface 112. In addition, the conductive pad disposed on the second surface 112 may be coupled to the first solder pad 12 disposed on the first surface 111 by a conductor 13 (shown in FIG. 14) embedded in the first body 11 of the first substrate 1.

As described above, referring to FIG. 5 and FIG. 6, FIG. 6 is an exploded view of the cable assembly according to the first embodiment of the present disclosure. The second substrate 2 may be correspondingly disposed on the first substrate 1. The second substrate 2 may include a second body 21, a second solder pad 22 disposed on the second body 21 and corresponding to the first solder pad 12, and an accommodating portion 20 corresponding to the second solder pad 22. In addition, in the configuration of FIG. 5 and FIG. 6, the second substrate 2 may further include a third solder pad 23, and the third solder pad 23 may be disposed on the second body 21 and coupled to the second solder pad 22. Further, the third solder pad 23 may also be disposed corresponding to the first solder pad 12. Further, the second body 21 includes a third surface 211, a fourth surface 212 corresponding to the third surface 211, and a connecting surface 213 connected to the third surface 211 and the fourth surface 212. Furthermore, the third solder pad 23 may be disposed on the third surface 211, the second solder pad 22 may be disposed on the connection surface 213, and the accommodating portion 20 may correspond to the connection surface 213. In addition, it is worth mentioning that a plurality of conductive pads (not shown) may also be disposed on the fourth surface 212, but the present disclosure is not limited by the inclusion of the conductive pads on the fourth surface 212. Further, in the first embodiment, the accommodating portion 20 may be disposed on one side of the second body 21 and in the form of a groove-shaped opening relative to the second substrate 2. That is to say, the groove-shaped opening can extend through the third surface 211 and the fourth surface 212, but the present disclosure is not limited thereto.

For example, the first substrate 1 and the second substrate 2 may be a printed circuit board (PCB) or a flexible printed circuit board (FPCB), respectively, and may also be a single layer board or a multi-layer board. In addition, for example, the first solder pad 12, the second solder pad 22, and/or the third solder pad 23 may be pads or metal layers disposed on the first body 11 and the second body 21 of the first substrate 1 and the second substrate 2, respectively. In addition, the wire 3 provided by the present disclosure is exemplified as a coaxial cable, and the inner conductor (soldering portion 30) of the coaxial cable and the accommodating portion 20 of the second substrate 2 are exemplified as being welded to each other. However, in other embodiments, the wire 3 may also be other wires that need to be soldered, such as, but not limited to a single core wire or a stranded wire, but the present disclosure is not limited thereto. It should be noted that the above example only is one of the possible implementations and should not be construed as limiting the present disclosure.

Figure 6:
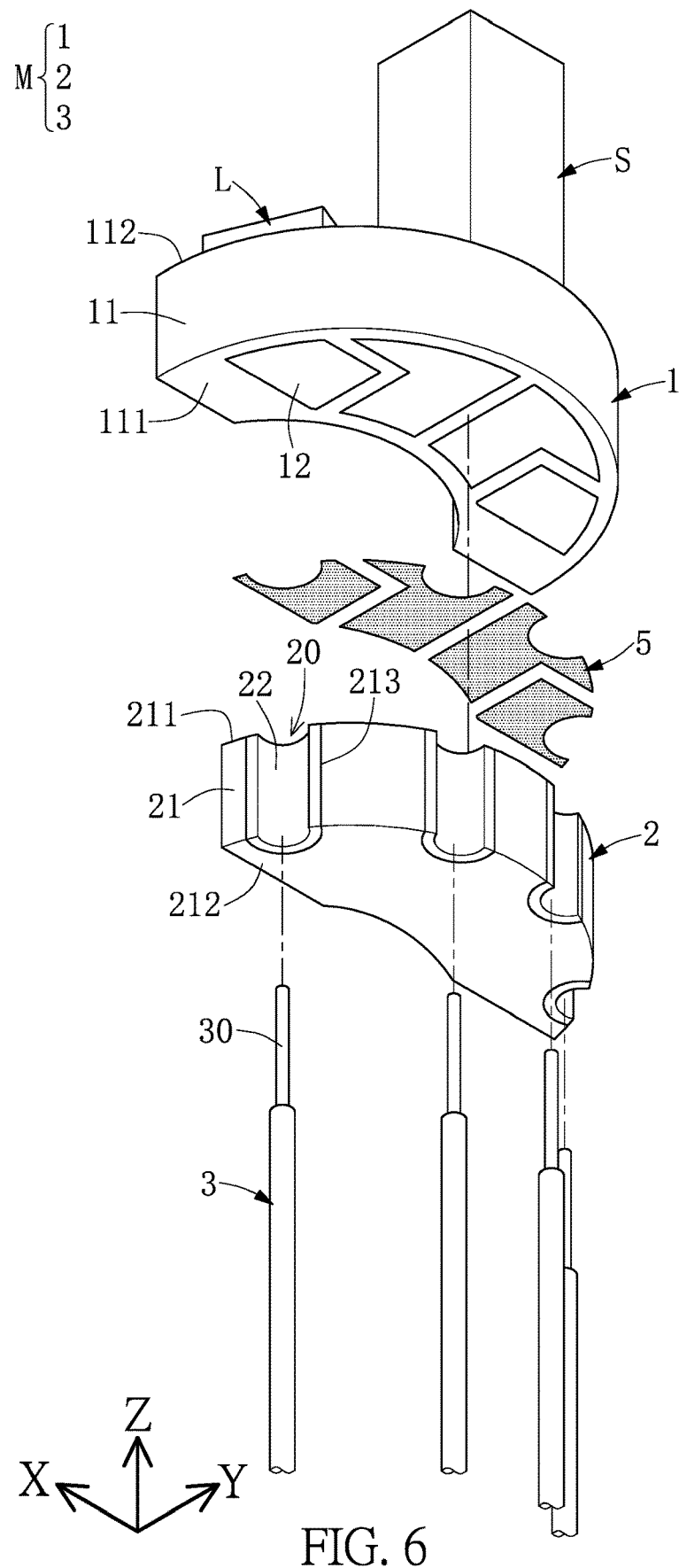
FIG. 6 is another exploded view of the cable assembly according to the first embodiment of the present disclosure.
Figure 7:
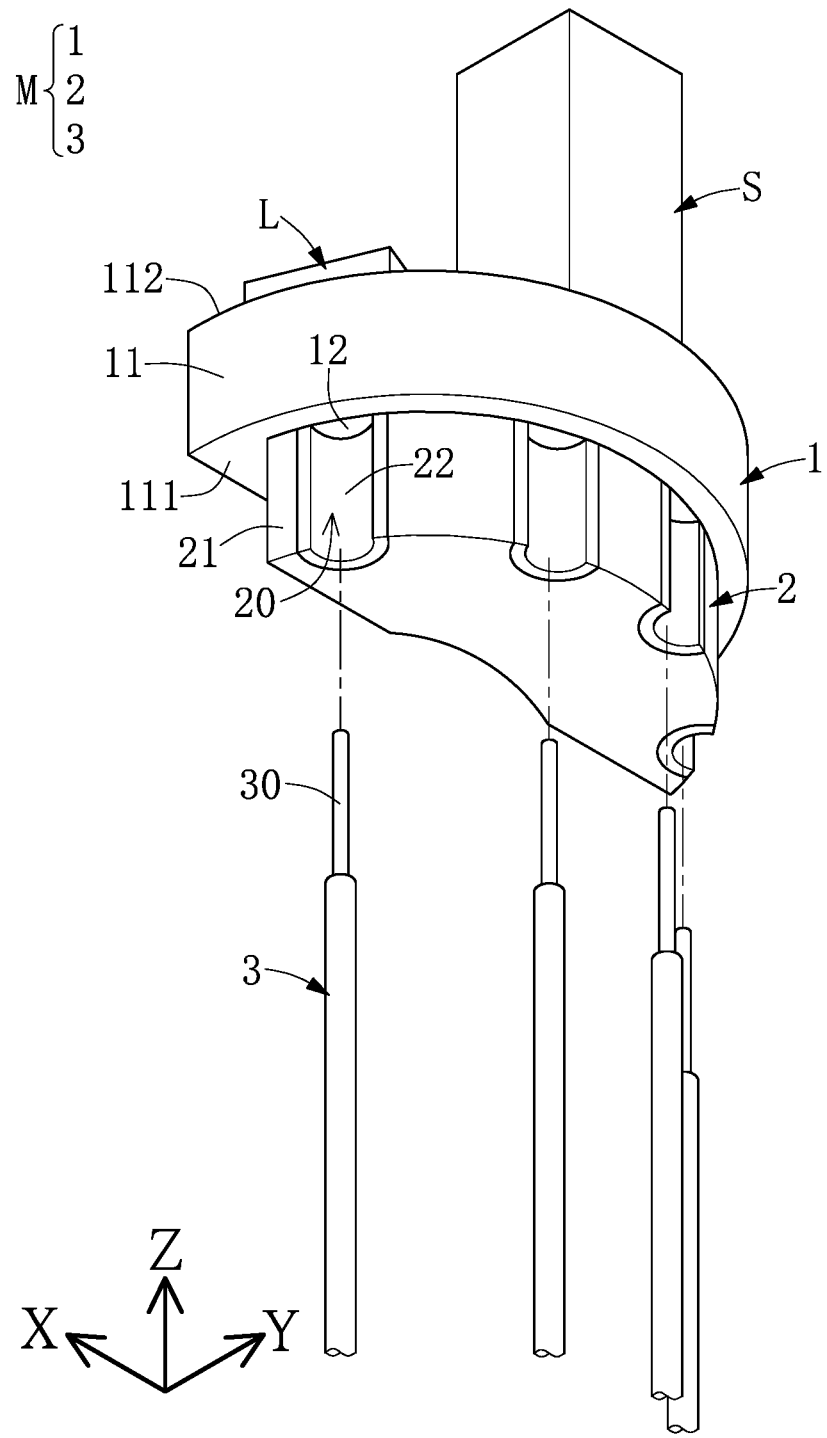
FIG. 7 is another perspective exploded view of the cable assembly according to the first embodiment of the present disclosure.

Next, referring to FIG. 5, FIG. 6, and FIG. 7, FIG. 7 is a perspective exploded view of the cable assembly according to the first embodiment. In the configuration of FIG. 5 to FIG. 7, since the second substrate 2 is further disposed with a third solder pad 23, a second solder 5 (such as, but not limited to, solder or solder paste) may be further provided, and the second solder 5 may correspond to the first solder pad 12 and the third solder pad 23 at the same time. Then, the first solder pad 12 of the first substrate 1 and the third solder pad 23 of the second substrate 2 are soldered to each other by a surface mount technology (SMT), so that the first solder pad 12 and the second solder pad 22 are coupled to each other by the second solder 5 and the third solder pad 23. In other words, the second solder 5 may be disposed between the first solder pad 12 and the third solder pad 23 so that the first substrate 1 and the second substrate 2 are coupled to each other.

Figure 8:
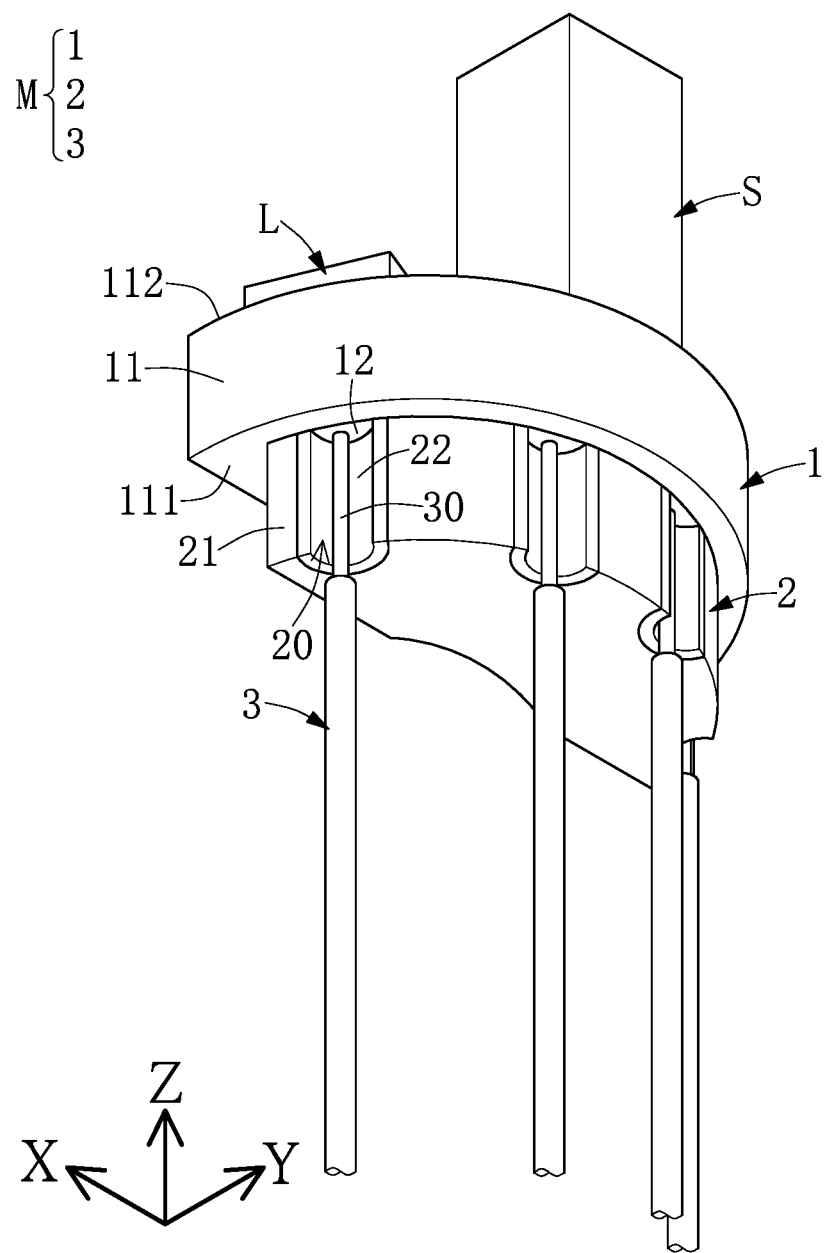
FIG. 8 is another perspective exploded view of the cable assembly according to the first embodiment of the present disclosure.

Next, referring to FIG. 4 and FIG. 8, FIG. 8 is a perspective exploded view of the cable assembly according to the first embodiment of the present disclosure. The wire 3 includes a soldering portion 30 disposed in the accommodating portion 20. The first solder 4 is disposed in the accommodating portion 20 and between the soldering portion 30 and the second solder pad 22. The soldering portion 30 and the second solder pad 22 are coupled to each other by soldering of the first solder 4, so that the wire 3 and the second substrate 2 are coupled to each other. For example, the first solder 4 may be soldered between the soldering portion 30 and the second solder pad 22 by a solder gun, a soldering iron, a laser soldering process or a drag soldering process to bond the soldering portion 30 and the second solder pad 22, but the present disclosure is not limited thereto.

As described above, referring to FIG. 4 and FIG. 8, in the present disclosure, a lengthwise direction of the soldering portion 30 of the wire 3 (or a length direction, i.e., the Z direction in the figures) is substantially parallel to an extended direction (Z direction) of the accommodating portion 20. For example, the extended direction of the accommodating portion 20 is the direction towards which the vertical projection of the accommodating portion 20 relative to the first surface 111 and the second surface 112 of the second body 21 is oriented.

Figure 9:
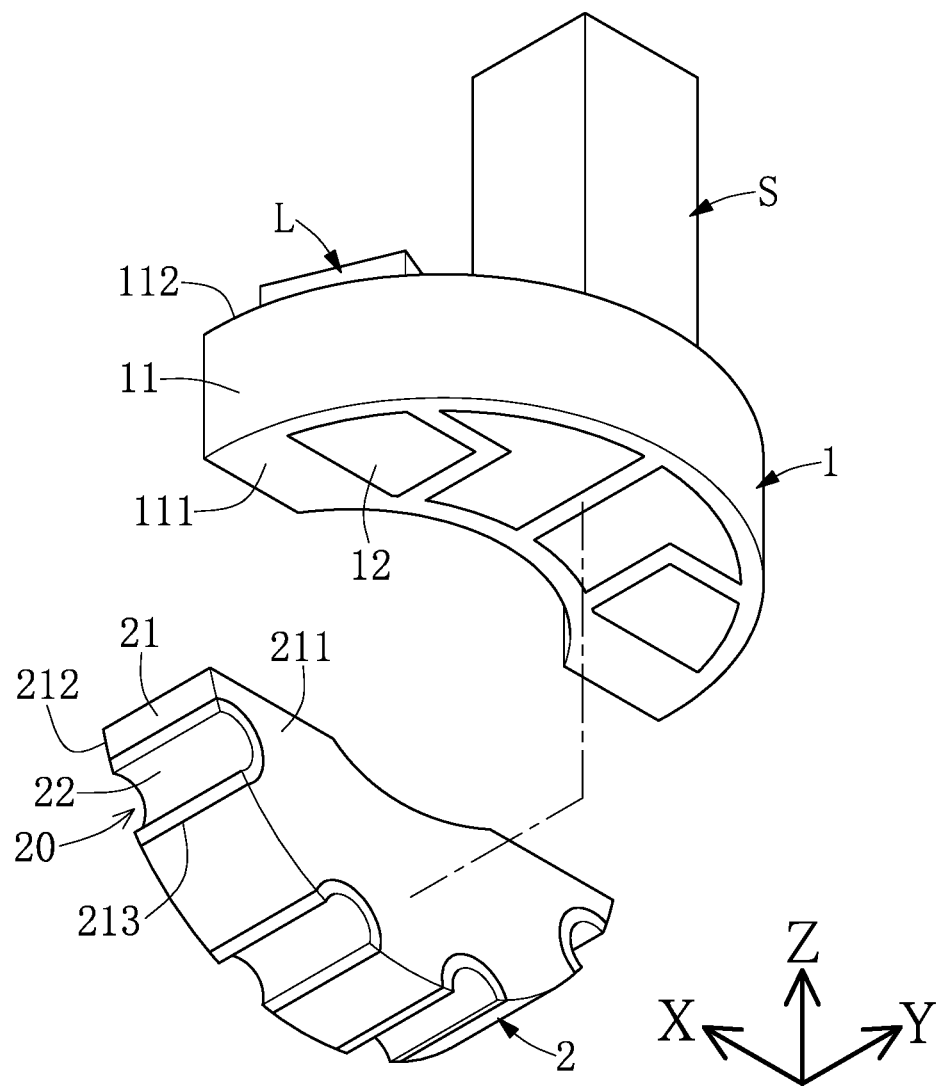
FIG. 9 is another perspective exploded view showing another configuration of the cable assembly according to the first embodiment of the present disclosure.

Next, referring to FIG. 5 and FIG. 9, FIG. 9 is another perspective exploded view showing another configuration of the cable assembly according to the first embodiment of the present disclosure. Comparing FIG. 5 with FIG. 9, in the configuration of FIG. 9, the second substrate 2 may not be disposed with the third solder pad 23. Further, in the configuration of FIG. 9, in order to couple the first solder pad 12 on the first substrate 1 and the second solder pad 22 on the second substrate 2 with each other, the first surface 111 of the first substrate 1 and the third surface 211 of the second substrate 2 are abutted against each other, and then the soldering portion 30 of the wire 3 is disposed in the accommodating portion 20, and the molten first solder 4 is disposed in the accommodating portion 20 and between the soldering portion 30 and the second solder pad 22 so that the cured first solder 4 is coupled to the wire 3 and the second substrate 2. In addition, in the configuration of FIG. 9, the first solder 4 is also disposed between the first solder pad 12 and the second solder pad 22 to couple the first substrate 1 and the second substrate 2 with each other. Therefore, in the first embodiment, the first solder pad 12 and the second solder pad 22 may be coupled to each other by at least one of the first solder 4 and the second solder 5.

It should be noted that the coupling in the present disclosure may be a direct connection or an indirect connection, or a direct electrical connection or an indirect electrical connection, and the present disclosure is not limited thereto.

Second Embodiment

Figure 10:
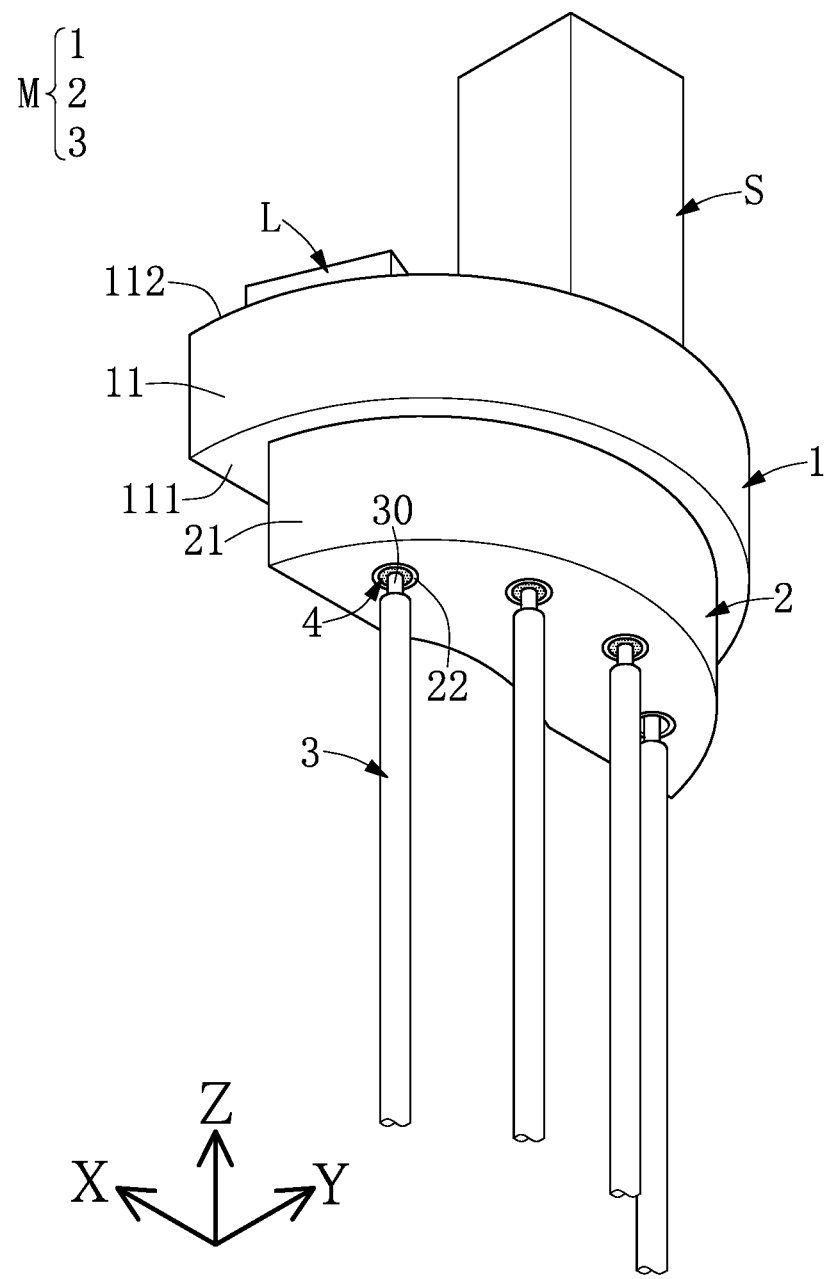
FIG. 10 is a perspective view of the cable assembly according to a second embodiment of the present disclosure.

Referring to FIG. 10, FIG. 10 is a perspective view of the cable assembly according to a second embodiment of the present disclosure. Comparing FIG. 10 with FIG. 4, the greatest difference between the second embodiment and the first embodiment of the present disclosure is that the position and manner that the accommodating portion 20 of the second embodiment is disposed are different from those of the first embodiment. It should be noted that the structural features and positional correspondences of the first substrate 1 and the wire 3 in the cable assembly M of the second embodiment are similar to those of the first embodiment, and details thereof will not be described again herein. Furthermore, the cable assembly M provided by the second embodiment can also be applied to the endoscope device U in the first embodiment.

Figure 11:
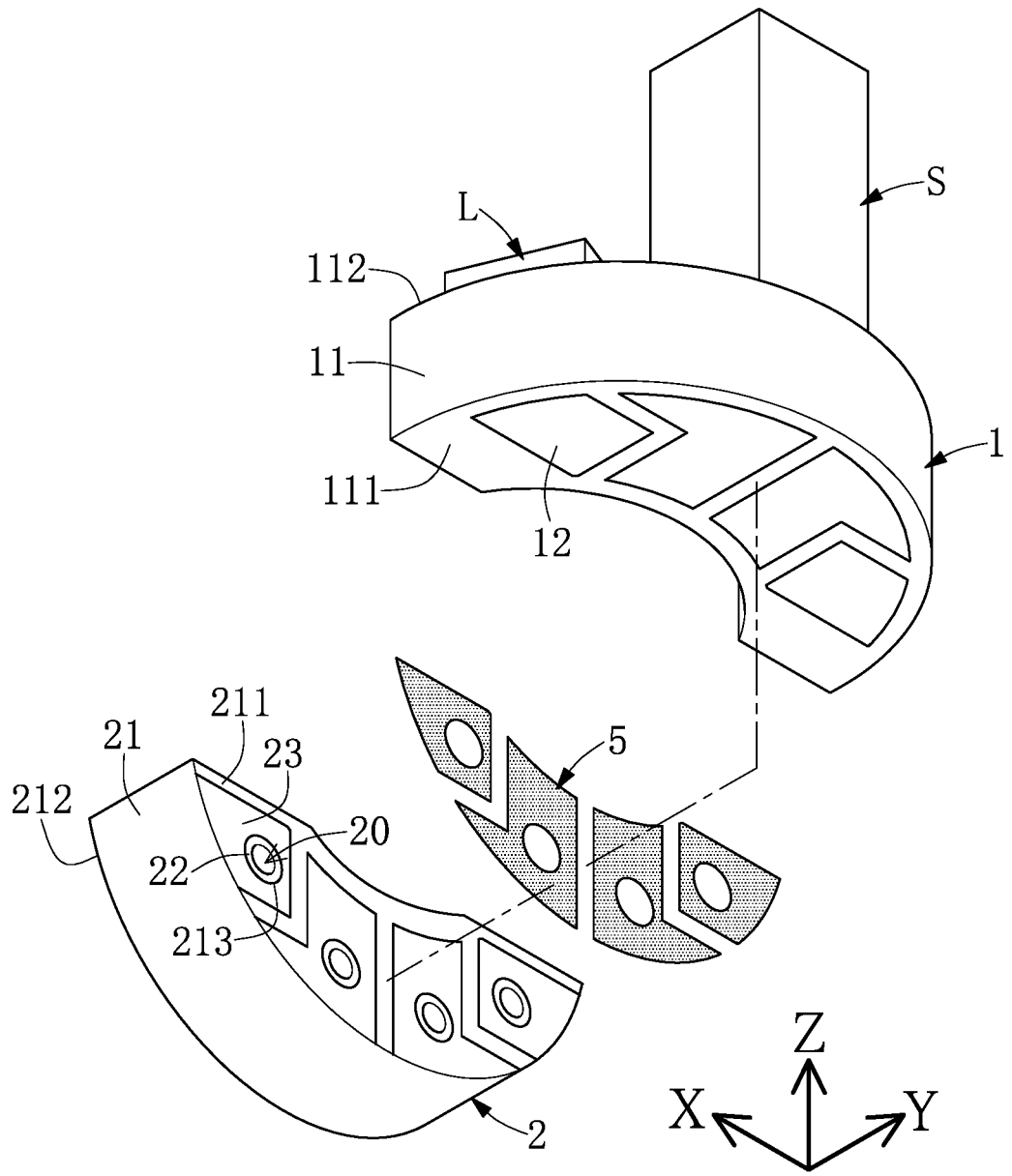
FIG. 11 is a perspective exploded view of the cable assembly according to the second embodiment of the present disclosure.

Based on the above, and referring to FIG. 10 and FIG. 11, FIG. 11 is a perspective exploded view of the cable assembly according to the second embodiment of the present disclosure. The second substrate 2 is correspondingly disposed on the first substrate 1. The second substrate 2 includes a second body 21, a second solder pad 22 disposed on the second body 21 and corresponding to the first solder pad 12, and a second body 21 disposed on the second body 21 and coupled to the second solder pad 22. In addition, the third solder pad 23 is disposed corresponding to the first solder pad 12. Further, the second body 21 includes a third surface 211, a fourth surface 212 corresponding to the third surface 211, and a connection surface 213 connected to the third surface 211 and the fourth surface 212. Furthermore, the third solder pad 23 is disposed on the third surface 211, the second solder pad 22 is disposed on the connection surface 213, and the accommodating portion 20 corresponds to the connection surface 213. Further, in the second embodiment, the accommodating portion 20 extends through the third surface 211 and the fourth surface 212 in the form of a through hole, relative to the second substrate 2. That is, the second solder pad 22 is a via disposed in the second substrate 2, and the through hole extends through the third surface 211 and the fourth surface 212, but the present disclosure is not limited thereto.

Figure 12:
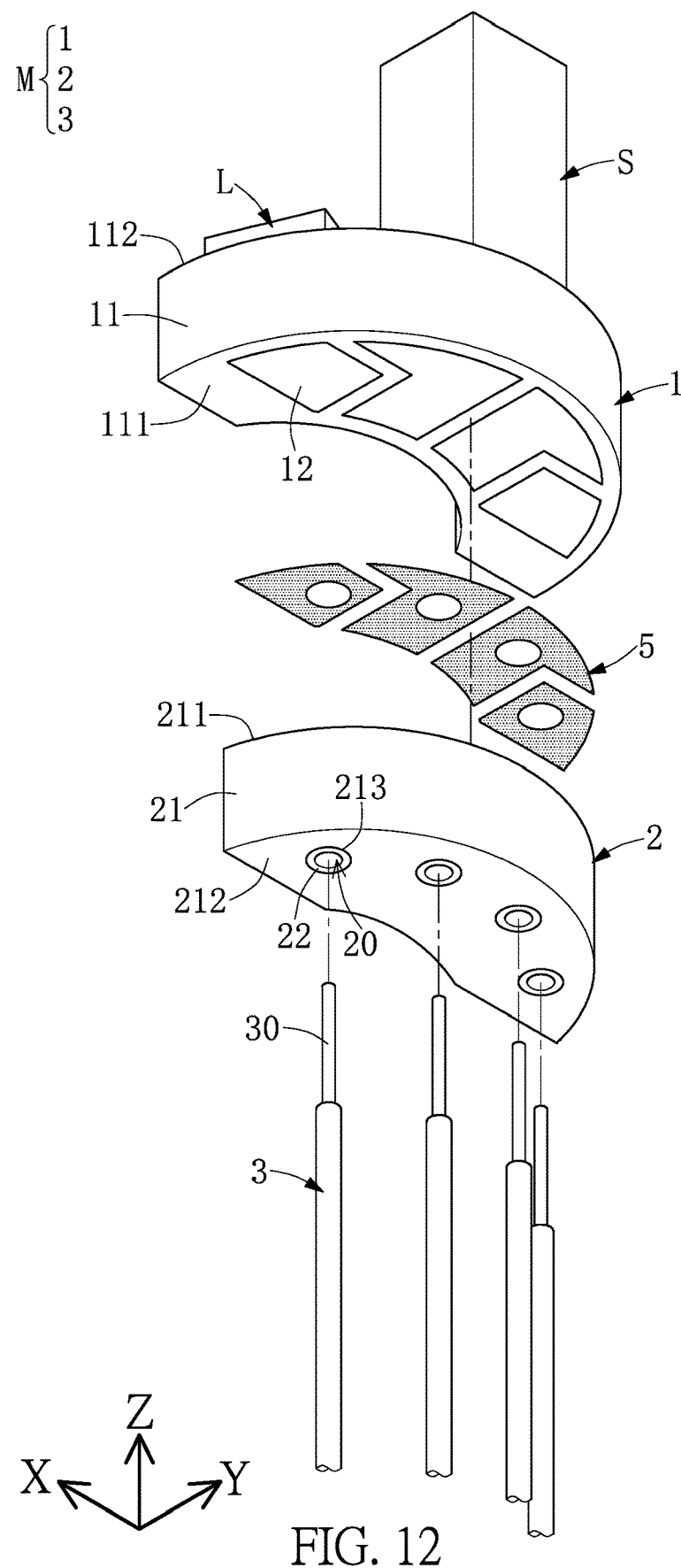
FIG. 12 is another perspective exploded view of the cable assembly according to the second embodiment of the present disclosure.
Figure 13:
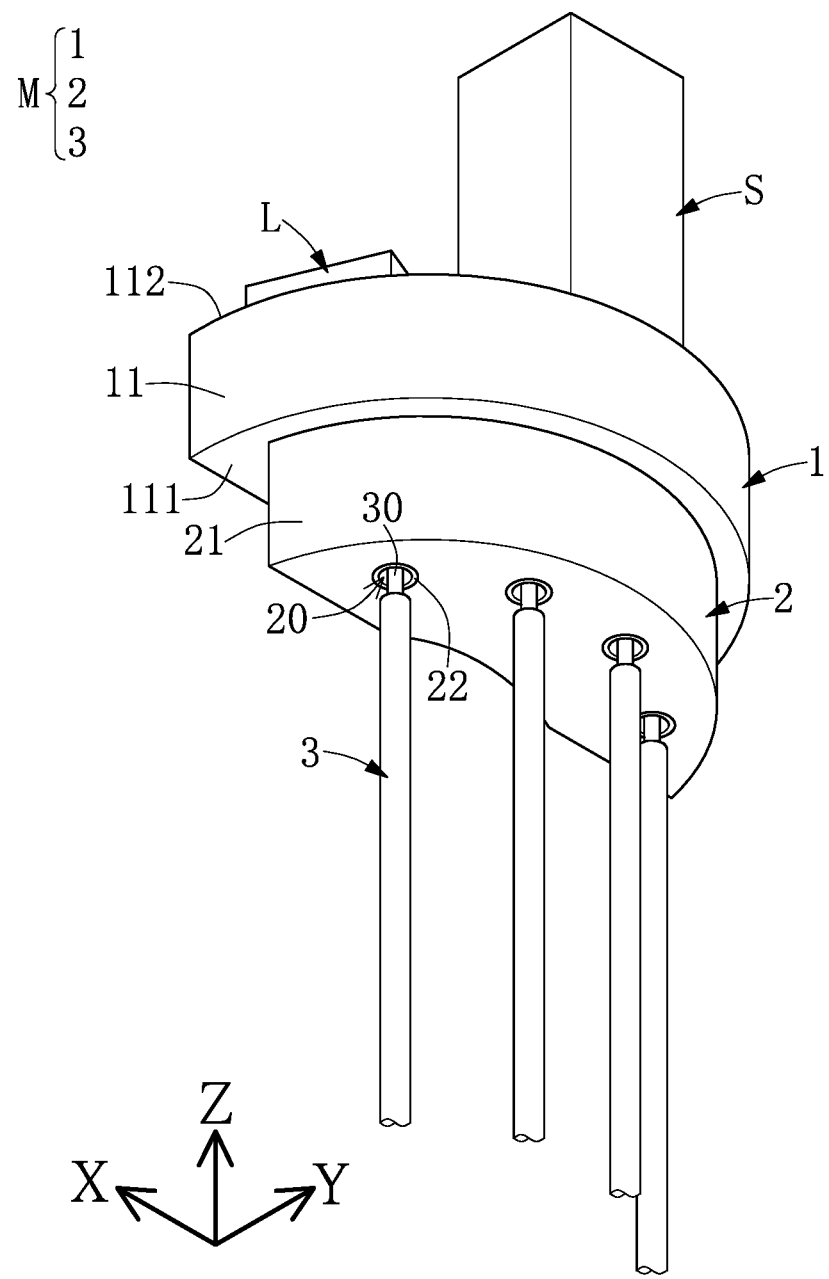
FIG. 13 is another perspective exploded view of the cable assembly according to the second embodiment of the present disclosure.

Next, referring to FIG. 11, FIG. 12 and FIG. 13, a second solder 5 is simultaneously disposed corresponding to the first solder pad 12 and the third solder pad 23. Then, the first solder pad 12 of the first substrate 1 and the third solder pad 23 of the second substrate 2 are soldered to each other by a surface mount technology (SMT), so that the first solder pad 12 and the second solder pad 22 are coupled to each other by the second solder 5 and the third solder pad 23. In other words, the second solder 5 is disposed between the first solder pad 12 and the third solder pad 23 so that the first substrate 1 and the second substrate 2 are coupled to each other.

Next, referring to FIG. 13 and FIG. 11, the soldering portion 30 of the wire 3 is disposed in the accommodating portion 20. Further, a lengthwise direction of the soldering portion 30 of the wire 3 (or a length direction, i.e., the Z direction in the figure) may be substantially parallel to an extended direction (Z direction) of the accommodating portion 20. In the present disclosure, the extended direction of the accommodating portion 20 is the direction towards which the vertical projection of the accommodating portion 20 relative to the first surface 111 and the second surface 112 of the second body 21 is oriented. Further, in the second embodiment, a lengthwise direction of the soldering portion 30 may be disposed substantially parallel to a central axis (not shown) of the through hole.

Figure 14:
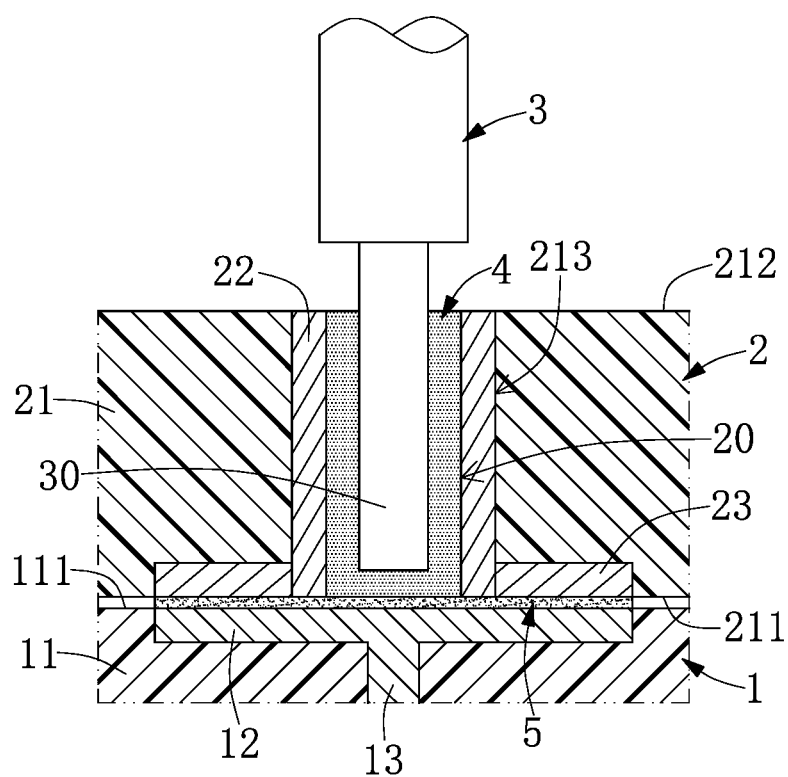
FIG. 14 is a cross-sectional view showing an accommodating portion of the cable assembly according to the second embodiment of the present disclosure.

Next, referring to FIG. 11 and FIG. 14, FIG. 14 is a cross-sectional view showing the accommodating portion of the cable assembly according to the second embodiment of the present disclosure. The first solder 4 may be disposed in the accommodating portion 20 and between the soldering portion 30 and the second solder pad 22. The soldering portion 30 and the second solder pad 22 may be coupled to each other by soldering of the first solder 4, so that the wire 3 and the second substrate 2 are coupled to each other. Therefore, in the second embodiment, the first solder pad 12 and the second solder pad 22 can be coupled to each other by the first solder 4 and the second solder 5.

Figure 15A:
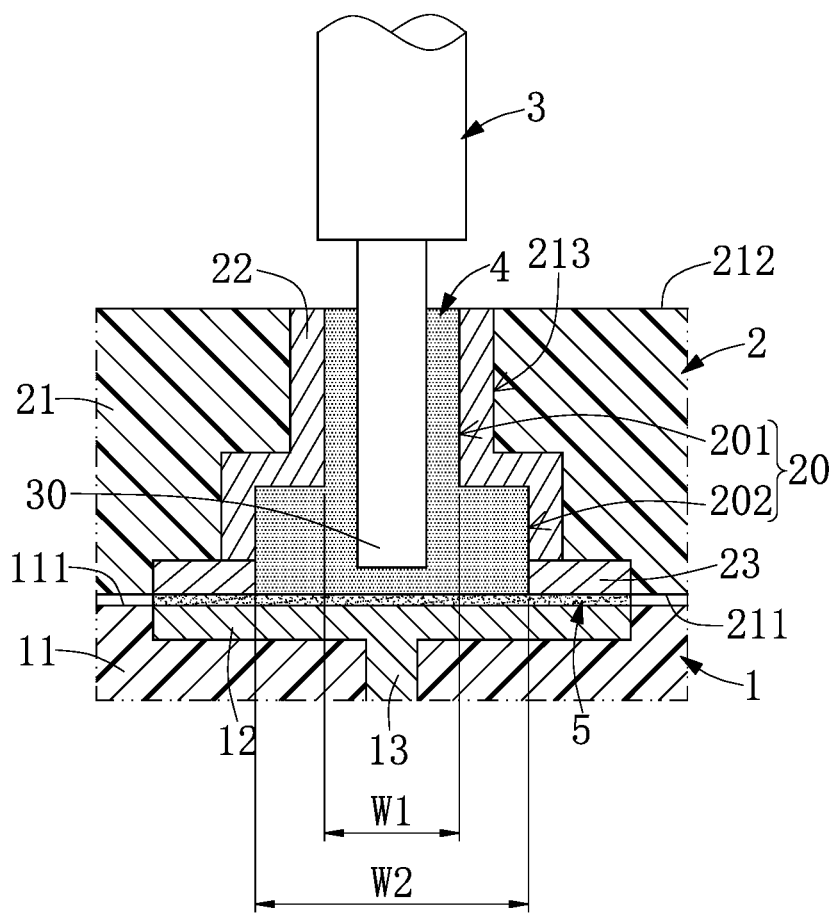
FIG. 15A and FIG. 15B are cross-sectional views showing the accommodating portion of a different embodiment of the cable assembly according to the second embodiment of the present disclosure.
Figure 15B:
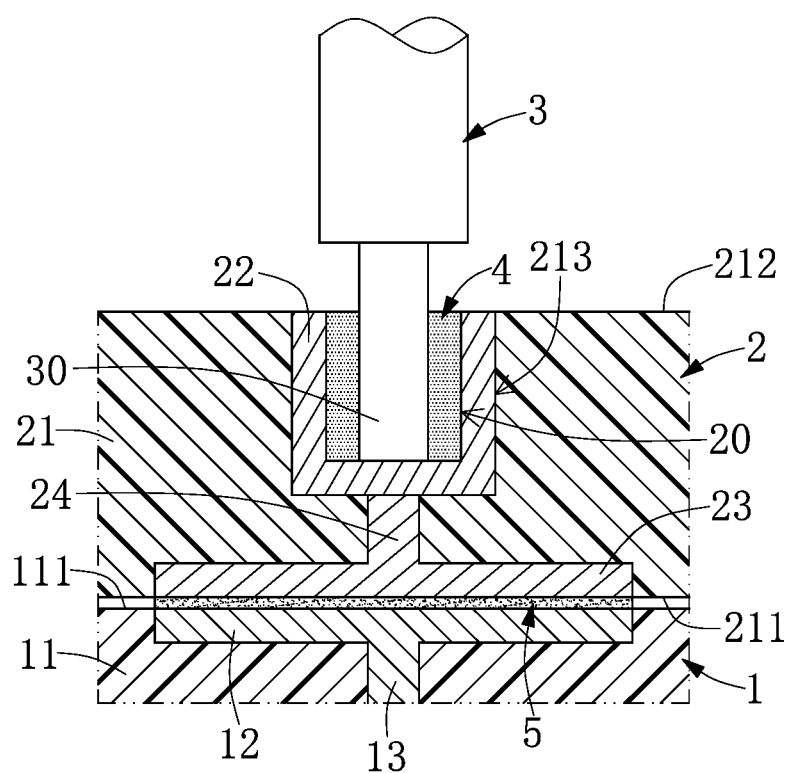

Referring to FIGS. 15A and 15B, FIG. 15A and FIG. 15B are cross-sectional views showing the accommodating portion of a different embodiment of the cable assembly according to the second embodiment of the present disclosure. In the configuration of FIG. 15A, the accommodating portion 20 is in the form of a through hole relative to the second substrate 2, and the accommodating portion 20 may include a first accommodating portion 201 and a second accommodating portion 202 connected to the first accommodating portion 201. The first accommodating portion 201 may be adjacent to the third surface 211, and the second accommodating portion 202 may be adjacent to the fourth surface 212. The first accommodating portion 201 may have a first diameter W1, the second accommodating portion 202 may have a second diameter W2, and the size of the first diameter W1 may be smaller than the size of the second diameter W2. However, it should be noted that although the size of the first diameter W1 is smaller than the size of the second diameter W2 in the drawings, in other embodiments, the size of the first diameter W1 may also be larger than the size of the second diameter W2, and the present disclosure is not limited thereto. However, in the present embodiment, the size of the first diameter W1 is smaller than the size of the second diameter W2, thereby being capable of accommodating a sufficient amount of the first solder 4, and preventing the first solder 4 from protruding from the third surface 211, so that the first substrate 1 and the second substrate 2 can be as close as possible to each other.

As described above, referring to FIG. 15A, in the configuration of FIG. 15A, since the size of the first diameter W1 is different from the size of the second diameter W2, the soldering portion 30 of the wire 3 may be first soldered to the second accommodating portion 202 by using the first solder 4, Thereafter, the second substrate 2 to which the wire 3 is soldered and the first substrate 1 are soldered to each other.

Next, in the embodiment of FIG. 15B, the accommodating portion 20 is in the form of a blind hole relative to the second substrate 2. Accordingly, the wire 3 can be coupled to the second solder pad 22 by using the first solder 4, and the second solder pad 22 can be coupled to the third solder pad 23 disposed on the third surface 211 through the conductor 24 embedded in the second body 21 of the second substrate 2. In addition, it is worth mentioning that in the embodiment of FIG. 15B, the second solder pad 22 can be extended to the fourth surface 212, but the present disclosure is not limited thereto. Moreover, in another configuration of FIG. 15A, the second solder pad 22 can extend onto the fourth surface 212.

In conclusion, one of the beneficial effects of the endoscope device U and the cable assembly M thereof of the present disclosure has the technical features of "the second substrate 2 being correspondingly disposed on the first substrate 1 and including a second body 21, a second solder pad 22 disposed on the second body 21 and corresponding to the first solder pad 12, and an accommodating portion 20 corresponding to the second solder pad 22," and "the first solder pad 12 and the second solder pad 22 being coupled to each other by at least one of a first solder 4 and a second solder 5, and the soldering portion 30 and the second solder pad 22 being coupled to each other by the first solder 4," so as to improve the reliability of the coupling effect between the wire 3 and the first substrate 1.

Furthermore, the first substrate 1 provided by the present disclosure is similar to a circuit board provided with an image sensor or a photosensitive element of the related art. In other words, the wire 3 can be firmly soldered to the second substrate 2 provided by the present disclosure, and the first substrate 1 and the second substrate 2 can be bonded to each other by surface adhesion or other soldering methods, thereby improving the reliability of the connection between the wire 3 and the first substrate 1.

Further, when the accommodating portion 20 is disposed on one side of the second body 21 and is in the form of a groove relative to the second substrate 2, the wire 3 can be more easily soldered on the accommodating portion 20 of the second substrate 2.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An endoscope device with a working channel, comprising:
    an image sensor configured to observe an internal environment of a target; and
    a cable assembly electrically connected to the image sensor and a plurality of conducting wires, the cable assembly comprising:
        a first substrate connected to the image sensor and including a plurality of first solder pads formed on a first bottom end of the first substrate;
        a second substrate including a plurality of receiving holes formed on a second bottom end of the second substrate, and the second substrate electrically connect to the plurality of first solder pads of the first substrate and the plurality of conducting wires via the plurality of receiving holes;
        an inner lateral side surface formed by the first substrate and the second substrate, and the inner lateral side surface matching an outer surface of the working channel, wherein a center of circle of the first substrate or the second substrate is misaligned to a center of circle of the working channel; and
        an outer lateral side surface being a stepped curved surface formed by the first substrate and the second substrate; wherein the plurality of receiving holes are recessed from a lower curved surface of the stepped curved surface formed by the second substrate, and a diameter of the second substrate is less than a diameter of the first substrate;
    wherein the first substrate and the second substrate are coupled to each other, and a plurality of inner conductors of the conducting wires are soldered to the second substrate.

2. The endoscope device according to claim 1, wherein shapes of the first substrate and the second substrate are both arc shaped, and radians of the first substrate and the second substrate are smaller than 2 $\pi$.

3. The endoscope device according to claim 1, wherein the first substrate and the second substrate are connected by solders positioned and aligned with the plurality of first solder pads of the first substrate.

4. The endoscope device according to claim 1, wherein the cable assembly has a symmetrical shape with respect to an axis of symmetry, and the image sensor is disposed on the axis of symmetry.

* * * * *